(12) United States Patent
Klostermann et al.

(10) Patent No.: US 7,725,194 B2
(45) Date of Patent: May 25, 2010

(54) TELEMETRY-BASED WAKE UP OF AN IMPLANTABLE MEDICAL DEVICE

(75) Inventors: Daniel Joseph Klostermann, Valencia, CA (US); Md. Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1086 days.

(21) Appl. No.: 11/215,369

(22) Filed: Aug. 30, 2005

(65) Prior Publication Data

US 2007/0049991 A1    Mar. 1, 2007

(51) Int. Cl.
*A61N 1/39*   (2006.01)
*A61N 1/00*   (2006.01)

(52) U.S. Cl. ........................... 607/60; 607/117
(58) Field of Classification Search ............... 607/60, 607/117; 713/310, 323–324; 380/270
See application file for complete search history.

(56) References Cited

U.S. PATENT DOCUMENTS

| | | | |
|---|---|---|---|
| 3,646,940 A | 3/1972 | Timm et al. | 128/421 |
| 3,724,467 A | 4/1973 | Avery et al. | 128/418 |
| 3,822,708 A | 7/1974 | Zilber | 128/419 R |
| 6,181,969 B1 | 1/2001 | Gord | 607/59 |
| 6,516,227 B1 | 2/2003 | Meadows et al. | 607/46 |
| 7,359,753 B2 * | 4/2008 | Bange et al. | 607/32 |

OTHER PUBLICATIONS

U.S. Appl. No. 11/138,632, filed May 26, 2005, Parramon et al.

\* cited by examiner

*Primary Examiner*—Mark W Bockelman
(74) *Attorney, Agent, or Firm*—Wong, Cabello, Lutsch, Rutherford & Brucculeri, LLP (57) ABSTRACT

A method for telemetry between an implantable medical device and an external programming component is disclosed. The telemetry circuitry of the implantable device is initially powered on for only a portion of the time needed to receive the entirety of a wake-up signal from the external component. During that time, only a first portion of the wake-up signal as received form the external component is checked against the implantable device's understanding of that first portion as stored in its memory. If the implantable device does not recognize the received first portion, powering on of the telemetry circuitry is terminated. However, if that first portion is recognized, then the implantable device continues to power on the telemetry circuitry to receive another (second) portion of the wake-up signal. If that received second portion is recognized, then the telemetry circuitry is further powered to receive a next (third) portion of the wake-up signal from the external component, etc., until the entirety of the wake-up signal is recognized by the implantable device as having been received.

10 Claims, 7 Drawing Sheets

TELEMETRY-BASED WAKE UP OF AN IMPLANTABLE MEDICAL DEVICE

FIELD OF THE INVENTION

The present invention relates generally to implantable medical devices, e.g., pulse generators used in a Spinal Cord Stimulation (SCS) systems or other types of neural stimulation systems. More particularly, the present invention relates to a telemetry scheme for establishing communication between an implantable stimulator device and an external component wishing to send data to the implantable stimulator device.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. patent application Ser. No. 11/177,503, filed Jul. 8, 2005, which is incorporated herein by reference in its entirety.

Spinal cord stimulation is a well-accepted clinical method for reducing pain in certain populations of patients. An SCS system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the EPG or RF transceiver is implanted. Alternatively, the electrode lead may directly connect with the IPG or RF transceiver. For examples of other SCS systems and other stimulation systems, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

Figure 1:
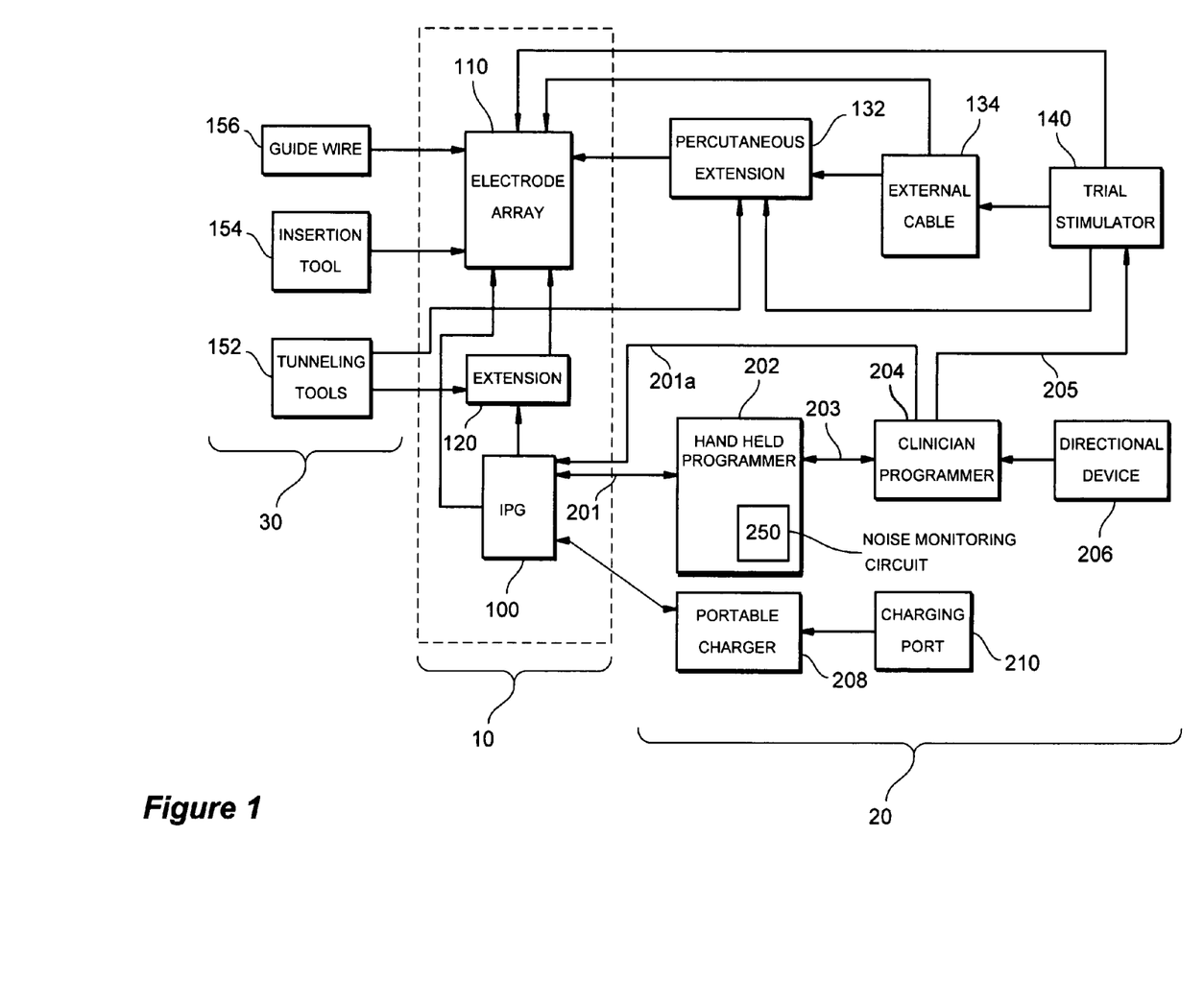
FIG. 1 shows a block diagram that illustrates exemplary implantable, external, and surgical components of a spinal cord stimulation (SCS) system that employs an implantable stimulator device in accordance with the present invention.
Figure 2:
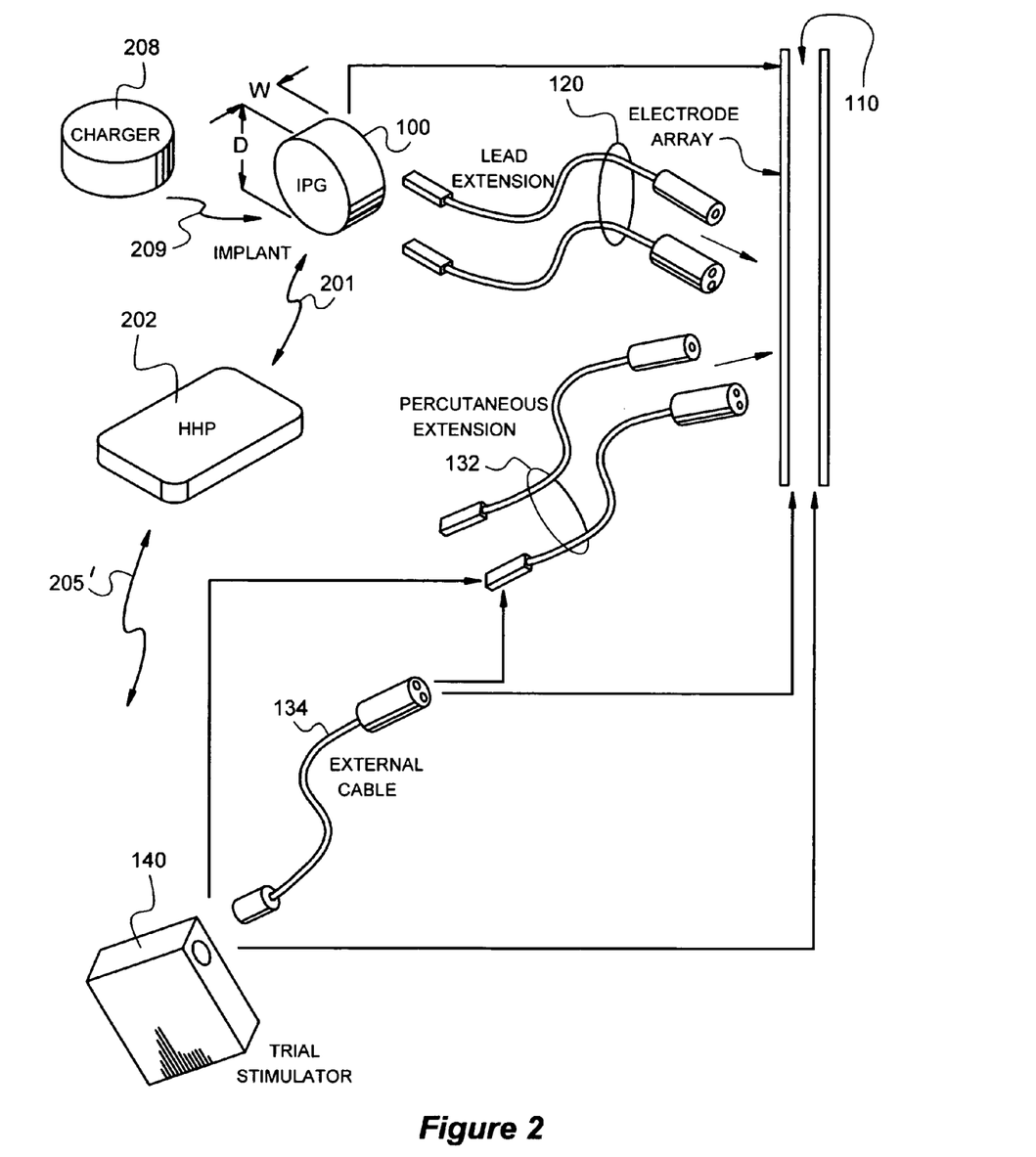
FIG. 2 shows various components of the SCS system of FIG. 1.
Figure 3:
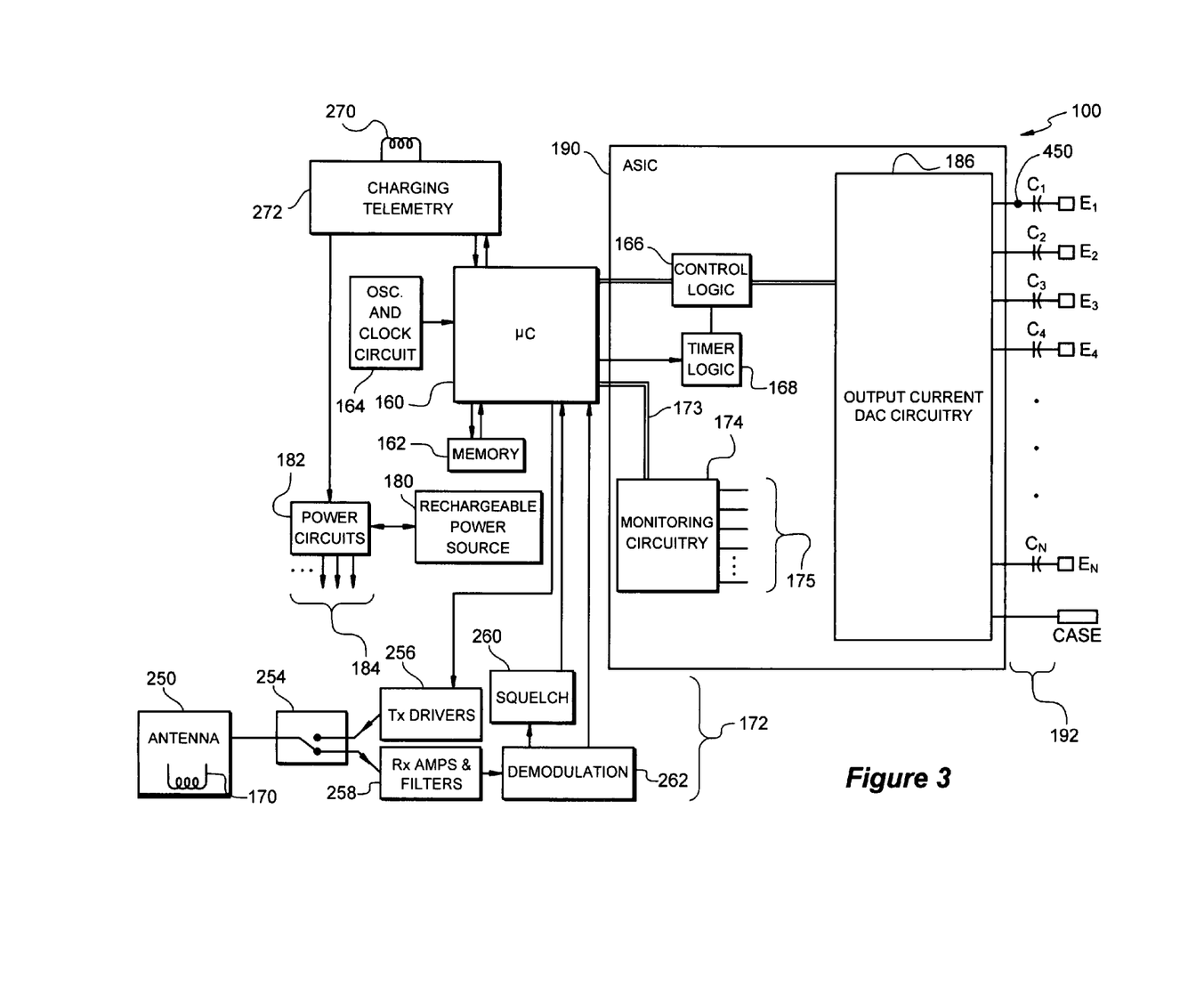
FIG. 3 shows a block diagram that illustrates the main components of one embodiment of an implantable stimulator device in which the invention can be used.

FIGS. 1-3 introduce various components of an exemplary SCS system, although further details will be explained more fully later. As particularly relevant to the present discussion, the SCS components comprise implantable components 10 (i.e., components implantable or implanted into a patient requiring therapy) and external components 20 (i.e., components external to the patient but which work in conjunction with the internal components 10). As seen in FIG. 1, the implantable components 10 include an implantable pulse generator (IPG) 100, which may comprise a rechargeable, multi-channel, telemetry-controlled, pulse generator. The external components 20 include a remote control 202, otherwise known as a hand-held programmer (HHP) 202, which may be used to control the EPG 100 via a suitable non-invasive communications link 201, e.g., an RF link. Such control allows the IPG 100 to be turned on or off, and generally allows stimulation parameters, e.g., pulse amplitude, width, and rate, to be set within prescribed limits. Detailed, system-level programming of the IPG 100 may additionally be accomplished through the use of an external clinician's programmer (CP) 204, which may also be hand-held and which may be coupled to the IPG 100 directly via an RF link 201a or indirectly using the HHP 202 as an intermediary. These RF links 201, 201a are preferably two-way links that can be used to send data to (i.e., control) the IPG 100, or to receive data from the IPG 100.

Such RF telemetry between the HHP 202 or CP 204 and the IPG 100 is supported via circuitry in the IPG 100, as shown in FIG. 3. Among other components and circuitry which will be described in further detail later, the IPG 100 comprises RF-telemetry circuitry 172, which receives RF telemetry data from the external components 20 (such as desired IPG operating parameters) and which sends RF telemetry data to the external components 20 (e.g., to allow the IPG 100's operating parameters to be verified, to allow the IPG 100's identification number to be reported, etc.).

Figure 5:
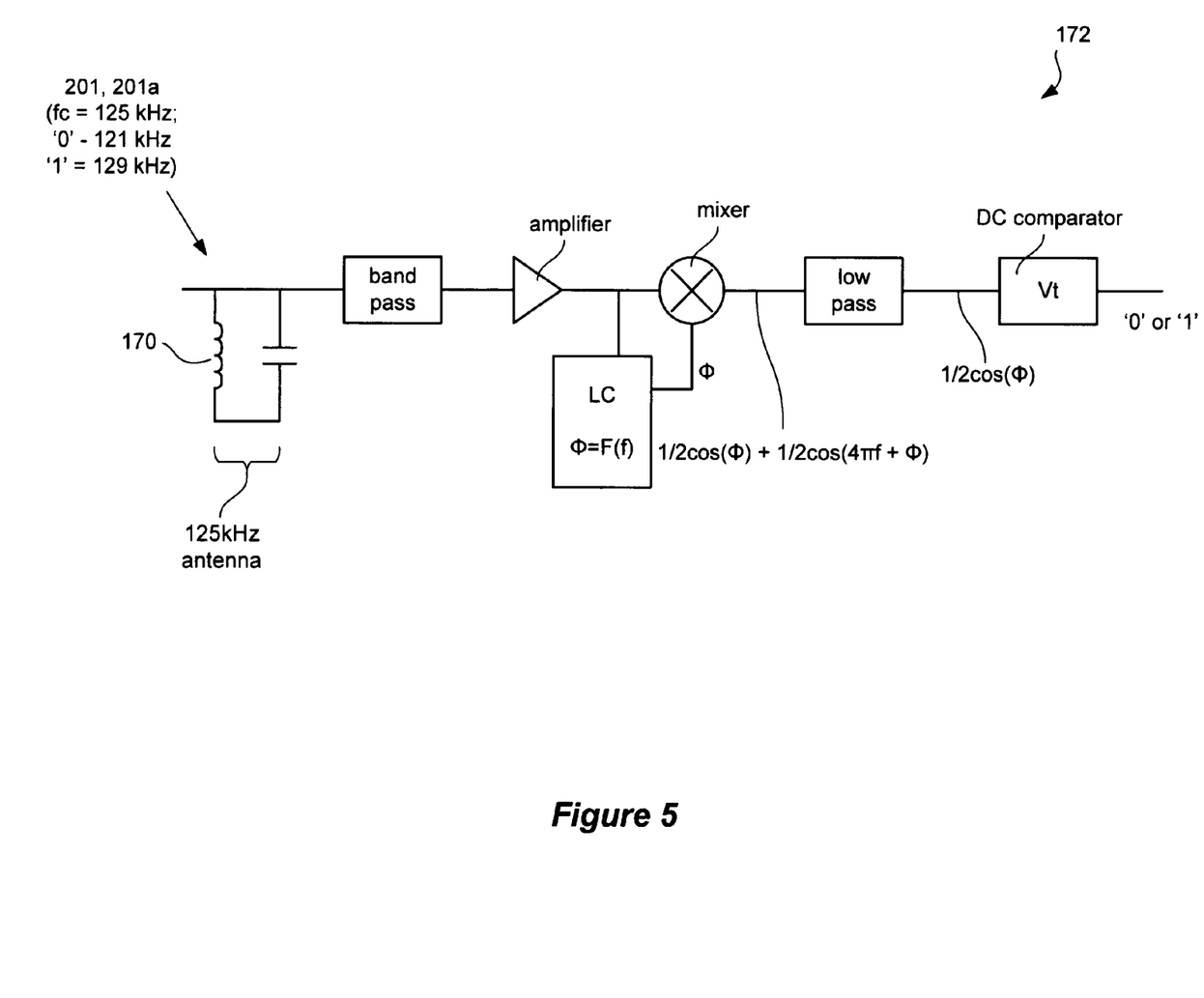
FIG. 5 illustrates the RF-telemetry circuitry used in an implantable stimulator and which can benefit from use of embodiments of the invention, and specifically shows the demodulation circuitry.

In recognition of the fact that the RF telemetry through links 201 and 201a would generally comprise use of a modulated carrier, RF-telemetry circuitry 172 would preferably include demodulator circuitry 262. Exemplary frequency demodulation circuitry useable in an IPG 100, as well as other components of the RF-telemetry circuitry 172, is shown in FIG. 5. What is shown for simplicity is an analog FM demodulation circuit, but one skilled in the art will recognize that it can be implemented digitally as well, and preferably would be implemented digitally in an implantable stimulator application. (In a digital implementation, some of the circuit elements shown would not be used, such as the LC circuit and mixer).

The operation of the demodulation circuitry is known to one skilled in the art, and hence is only briefly described. Essentially, data is sent to the demodulation circuitry (e.g., via RF links 201, 201a) as a sequence of bits represented by a variance in frequency (121 kHz, 129 kHz) from a center carrier frequency ($f_c$=125 kHz). After passing the received signal through a band pass filter to remove frequencies outside of the frequency range of interest, a phase shift (φ) is induced in the received signal via an LC circuit for example, in which the phase shift is a function of the frequency of the received signal. By mixing the phase shifted signal with the original received signal, and sending the result through a low pass filter to remove high-frequency components, a voltage (proportional to ½ cos(φ)) is generated which is compared to a threshold to determine whether the received signal comprised a 121 kHz signal (a logical '0') or a 129 kHz signal (a logical '1'). As noted earlier, digital demodulation is logical in an implantable medical device application, and could for example comprise use of the QFAST RF protocol, which supports bi-directional telemetry at, e.g., 8 Kbits/second. (QFAST stands for "Quadrature Fast Acquisition Spread Spectrum Technique," and represents a known and viable approach for modulating and demodulating data).

Regardless of whether an IPG 100 is powered by a non-rechargeable battery, or is powered by a battery rechargeable via an RF energy source (e.g., charger 208, FIG. 1), or is solely powered via an RF energy source, power consumption in an IPG is preferably kept to a minimum. For example, in the case of an IPG with a rechargeable battery, lower power consumption equates to longer periods in which the EPG can be used to provide stimulation between charges.

Telemetry procedures such as those just described can affect power consumption in an IPG 100. An IPG 100, regardless of whether it is currently providing stimulus to the patient in which it is implanted, needs to be ready for the possibility that an external component 20 (e.g., HHP 202 or CP 204) wishes to communicate with it, and hence must "listen" for relevant telemetry from the external component. Because power consumption in an external component is generally less critical (because it is external to the patient; because it can be plugged in or easily provided with fresh batteries, etc.), the external component can repeatedly broadcast its desire to communicate with the IPG, and then wait for the IPG to respond before sending its command to the IPG. In other words, the external component may broadcast nearly continually, aside from short periods to listen for a response from the IPG. This can be thought of as a "handshaking" or "wake up" procedure initiated by the external component, in which a wake-up signal is broadcast by the external component.

But such a handshaking approach necessitates that the IPG 100, and specifically the RF-telemetry circuitry 172, be powered by the IPG 100, because only when such circuitry 172 is powered can the IPG 100 recognize the wake-up signal from the external component and in turn telemeter an acknowledgment back to the external component. Ideally therefore, the RF-telemetry circuitry 172 would be powered by the IPG 100 at all times so that the IPG 100 could recognize an external component's wake-up signal immediately. But this is not practical, especially considering the relative infrequency that an external component might wish to communicate with an IGP 100. In short, keeping the RF-telemetry circuitry 172 powered at all times is not an efficient solution, as it drains too much power from the IPG 100.

In recognition of this fact, a procedure may be employed in which the RF-telemetry circuitry 172 is only occasionally powered by the IPG 100, for example, once every few seconds for a "window" of time comprising a number of milliseconds. While such an approach sacrifices immediacy in the IPG 100's recognition of the broadcast wake-up signal, it allows the RF-telemetry circuitry 172 to be powered only a fraction of the time, i.e., during the several millisecond "power-on window." This saves power, while still allowing the external component's broadcast wake-up signal to be eventually recognized and responded to by the IPG 100.

But even this procedure is potentially wasteful of power in the IPG. This is because the power-on window generally needs to be on for the entire length of time that it would take to receive a valid wake-up signal from the external component. In this regard, recognize that a broadcasted wake-up signal from an external component would generally comprise a serial stream of binary bits. Assume for example that the RF-telemetry circuitry 172 must recognize (i.e., demodulate) a certain number of bits in this sequence before acknowledging the wake-up signal and responding in kind with an acknowledgment. Such a scheme would dictate that the power-on window be active for the entirety of the time it would take to receive the number of bits that the IPG 100 must recognize as the wake-up signal. For example, suppose each bit in the sequence is broadcast by the external component for approximately 250 microseconds, and that the IPG 100 is looking for a particular 12-bit sequence as the wake-up signal. This means it would take at least 3 milliseconds (250 microseconds times 12) for the IPG 100 to understand receipt of the entire wake-up signal, and hence that the RF-telemetry circuitry 172 must be powered for at least that long. Indeed, depending on when the IPG 100 powers on the RF-telemetry circuitry 172 relative to the start of the broadcasted wake-up signal, the IPG 100 might well need to keep the RF-telemetry circuitry 172 powered on for longer than 3 milliseconds to understand the beginning of the sequence and to then fully receive it.

Having the IPG 100 power on the RF-telemetry circuit 172 window for even a mere 3 milliseconds every second or so is still significant in terms of the power that is consumed by the IPG 100, particularly given that handshaking from the external components would occur relatively rarely. Accordingly, the implantable stimulator art, or more specifically the IPG or SCS system art, would benefit from telemetry techniques for handshaking between an external component and an IPG that are less wasteful of power. Such solutions are provided herein.

SUMMARY

A method for RF telemetry between an implantable medical device (e.g., an implantable stimulator device) and an external programming component is disclosed which minimizes power drain in the implantable stimulator. In a preferred embodiment, the RF-telemetry circuitry of the implantable stimulator is initially powered on for only a portion of the time needed for the implantable stimulator to receive the entirety of a wake-up signal from the external component. During such partial window, only a first portion of the wake-up signal as received from the external component is checked against the implantable stimulator's understanding of that first portion as stored in its memory. If the implantable stimulator does not recognize the received first portion as corresponding to the stored first portion of the wake-up signal, powering on of the RF-telemetry circuitry is terminated, and such circuitry is not again powered on until the next power-on period—for example, seconds later. However, if that first portion is recognized, then the implantable stimulator continues to power on the RF-telemetry circuitry to receive another (second) portion of the wake-up signal. If that received second portion is recognized as corresponding to the second portion of the wake-up signal as stored, then the RF-telemetry circuitry is further powered to receive a next (third) portion of the wake-up signal from the external component, etc., until the entirety of the wake-up signal is recognized by the implantable stimulator as having been received. Once the wake-up signal is fully recognized by the implantable stimulator, the implantable stimulator understands that the external component wishes to send data to it, and thus the implantable stimulator powers on the RF-telemetry circuit (and generally wakes up the implantable stimulator) as is sufficient to receive such data.

BRIEF DESCRIPTION OF THE DRAWINGS

The above and other aspects of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the telemetry-based aspects of the invention, the circuitry, structure, and function of an implantable stimulator device in which the disclosed telemetry-based improvements can be used is set forth for completeness. The disclosed implantable stimulator device may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from power-saving telemetry procedures. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc.

Turning first to FIG. 1, a block diagram is shown that illustrates the various components of an exemplary SCS system in which the invention may be used. These components may be subdivided into three broad categories: implantable components 10, external components 20, and surgical components 30. As seen in FIG. 1, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below in connection with FIG. 3 or 4, may comprise a rechargeable, multichannel, telemetry-controlled, pulse generator housed in a rounded high-resistivity titanium alloy case to reduce eddy current heating during the inductive charging process. The IPG 100 may provide electrical stimulation through a multiplicity of electrodes, e.g., sixteen electrodes $E_1$ through $E_{16}$, included within the electrode array 110.

In this regard, the IPG 100 may include stimulating electrical circuitry ("stimulating electronics"), a power source, e.g., a rechargeable battery, and a telemetry system, the latter of which is particularly relevant to embodiments of the disclosed invention. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the EPG 100 may be replaced when its power source fails or is no longer rechargeable.

As seen best in FIG. 2, and as also illustrated in FIG. 1, the electrode array 110 and its associated lead system typically interface with the implantable pulse generator (IPG) 100 via the lead extension system 120 just mentioned. The electrode array 110 may also be connected to an external trial stimulator 140, through the use of a percutaneous lead extension 132 and/or an external cable 134. The external trial stimulator 140 typically includes the same or similar pulse generation circuitry as does the EPG 100, and is used on a trial basis, e.g., for 7-10 days, after the electrode array has been implanted and prior to implantation of the IPG 100, to test the effectiveness of the stimulation that is to be provided.

Still with reference to FIGS. 1 and 2, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits. The HHP 202 may also be linked with the external trial stimulator 140 through another link 205', e.g., an infra red link. Detailed programming of the IPG 100 is preferably accomplished through the use of an external clinician's programmer (CP) 204 (FIG. 1), which may also be hand-held and which may be coupled to the IPG 100 directly via link 201a or indirectly through the HHP 202. An external charger 208, non-invasively coupled with the IPG 100 through link 209, e.g., an inductive link, allows energy stored or otherwise made available to the charger 208 to be coupled into the rechargeable battery housed within the IPG 100, as explained further below.

Turning next to FIG. 3, a block diagram is shown that illustrates the main components of one embodiment of an implantable pulse generator (IPG) 100 in which embodiments of the invention may be used. As seen in FIG. 3, the IPG includes a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals which allow the μC 160 to control the operation of the IPG in accordance with a selected operating program and stimulation parameters.

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. As noted earlier, the RF-telemetry circuitry 172 demodulates the signal it receives from the HHP 202 or CP 204 to recover the operating program and/or the stimulation parameters. More specifically, telemetry received at coil 170 is met by an LC-tuned antenna 250, where it passes through a transmit/receive switch 254 to amplifiers and filters 258 (see also FIG. 5). From there, the received signals are demodulated (262) using Frequency Shift Keying (FSK) demodulation for example, and the now-digitized and demodulated data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the data is modulated and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through telemetry circuitry 172 via coil 170.

The operating power for the IPG 100 may be derived from a rechargeable power source 180, which may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIG. 1). When placed near the IPG 100 (e.g., centimeters away), an electromagnetic field emanating from the portable charger 208 induces a current in charging coil 270 (even through a patient's skin). This current is then rectified and regulated to charge the battery 180. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the HHP 202. External programming software in the CP 204 is typically used to set parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode contact may be programmed to one of several discrete current levels, e.g., between 0 to 10 mA in steps of 0.1 mA. Also, the pulse width of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive charge associated with a given stimulus pulse is offset with an equal and opposite negative charge. Charge balance may be achieved through coupling capacitors $C_x$, which provide a passive capacitor discharge that achieves the desired charge-balanced condition. Alternatively, active biphasic or multiphasic pulses with positive and negative phases that are balanced may be used to achieve the needed charge balanced condition.

In short, the IPG 100 is able to individually control the currents at the N electrodes. Controlling the output current Digital-to-Analog Current (DAC) circuitry 186 using the microcontroller 160, in combination with the control logic 166 and timer logic 168, allows each electrode contact to be paired or grouped with other electrode contacts, including the monopolar case electrode, to control the polarity, amplitude, rate, pulse width and channel through which the current stimulus pulses are provided.

As shown in FIG. 3, much of circuitry included within the IPG 100 may be realized on a single application specific integrated circuit (ASIC) 190. This allows the overall size of the IPG 100 to be quite small, and readily housed within a suitable hermetically-sealed case. The IPG 100 may include N feedthroughs to allow electrical contact to be individually made from inside of the hermetically-sealed case with the N electrodes that form part of the lead system outside of the case.

As noted earlier, in use, the EPG 100 may be placed in a surgically-made pocket, e.g., in the abdomen or just at the top of the buttocks, and detachably connected to the lead system (comprising optional lead extension 120 and electrode array 110). While the lead system is intended to be permanent, the IPG 100 may be replaced should its power source fail, or for other reasons.

The telemetry features of the IPG 100 allow the status of the IPG to be checked as noted earlier. For example, when the HHP 202 and/or the CP 204 initiate a programming session with the IPG 100 (FIG. 1), the capacity of the battery is telemetered so that the external programmer can calculate the estimated time to recharge. Any changes made to the current stimulus parameters are confirmed through back-telemetry, thereby assuring that such changes have been correctly received and implemented within the implant system. Moreover, upon interrogation by the external programmer, all programmable settings stored within the implant system 10 may be uploaded to one or more external programmers.

Figure 4:
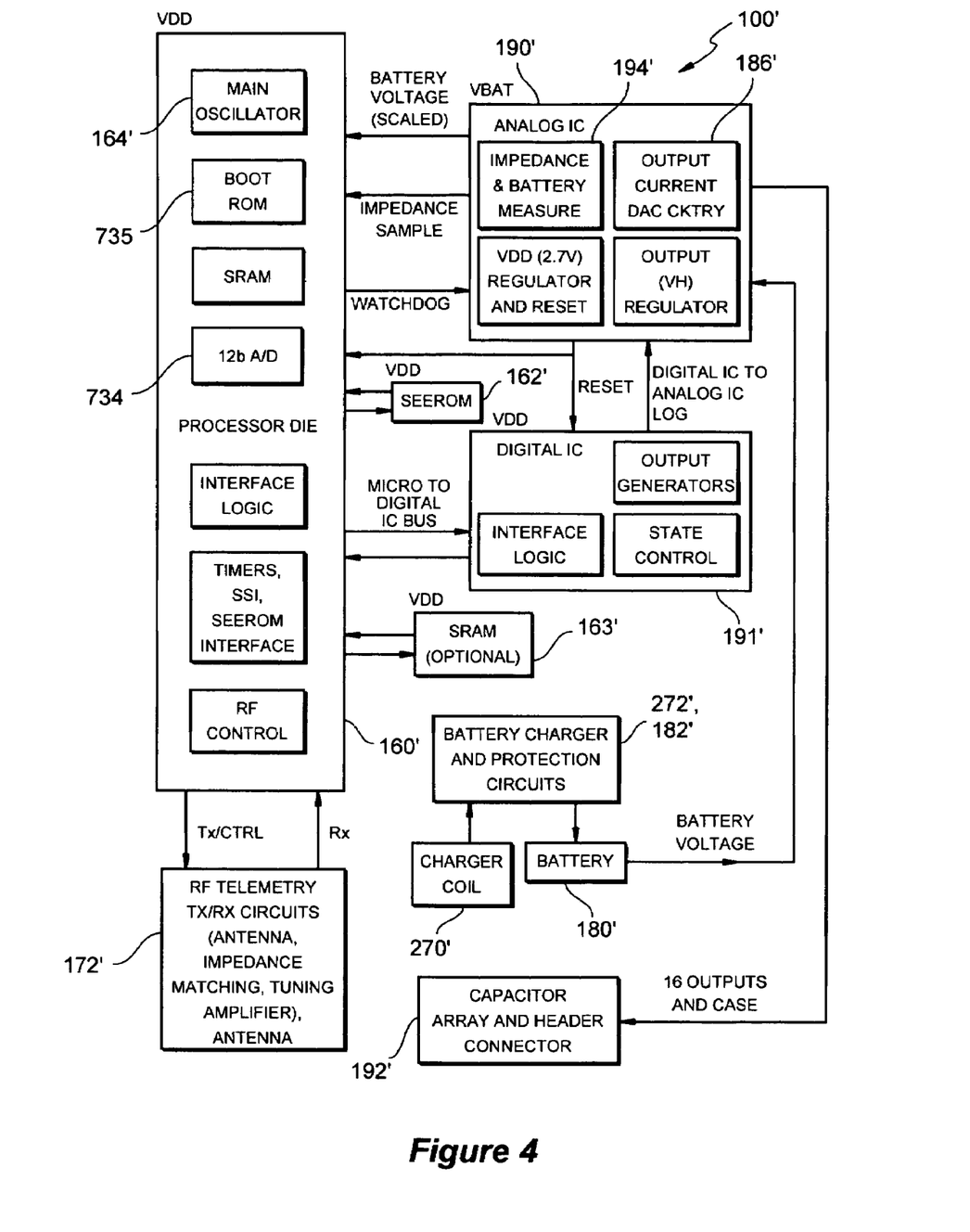
FIG. 4 shows a block diagram that illustrates another embodiment of an implantable stimulator device in which the invention can be used.

Turning next to FIG. 4, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 3. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_x$ and electrodes $E_x$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1$, $E_2$, $E_3$, ..., or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the power-saving telemetry features useable with such an implantable stimulator.

As noted earlier, for reasons of power savings, the RF-telemetry circuitry 172 may only periodically be powered on (e.g., every second or so) for a time window long enough (e.g., milliseconds) to assess whether a broadcast wake-up signal from an external component (HHP 202 or CP 204) is present. But, even if the power-on time window is relatively short in comparison to the frequency with which such window is established (e.g., milliseconds every second), power consumption in the IPG 100 is still significant. This is particularly true when it is recognized that an external component will wish to communicate with the IPG 100 relatively infrequently, and therefore that during most of these power-on windows the IPG 100 will listen in vain for no signal.

Accordingly, in preferred embodiments of the invention, the RF-telemetry circuitry of the IPG 100 is initially powered on for only a portion of the time needed for the IPG to receive the entirety of a wake-up signal from the external component. During such partial window, only a first portion of the wake-up signal as received form the external component is checked against the IPG 100's understanding of that first portion as stored in its memory. If the IPG does not recognize the received first portion as corresponding to the stored first portion of the wake-up signal, powering on of the RF-telemetry circuitry is terminated, and such circuitry is not again powered on until the next power-on period—for example, seconds later. However, if that first portion is recognized, then the IPG 100 continues to power on the RF-telemetry circuitry to receive another (second) portion of the wake-up signal. If that received second portion is recognized as corresponding to the second portion of the wake-up signal as stored, then the RF-telemetry circuitry is further powered to receive a next (third) portion of the wake-up signal from the external component, etc., until the entirety of the wake-up signal is recognized by the IPG 100 as having been received. Once the wake-up signal is fully recognized by the IPG 100, the IPG understands that the external component wishes to send data to it, and thus the IPG powers on the RF-telemetry circuit (and generally wakes up the IPG) as sufficient to receive such data.

Figure 6:
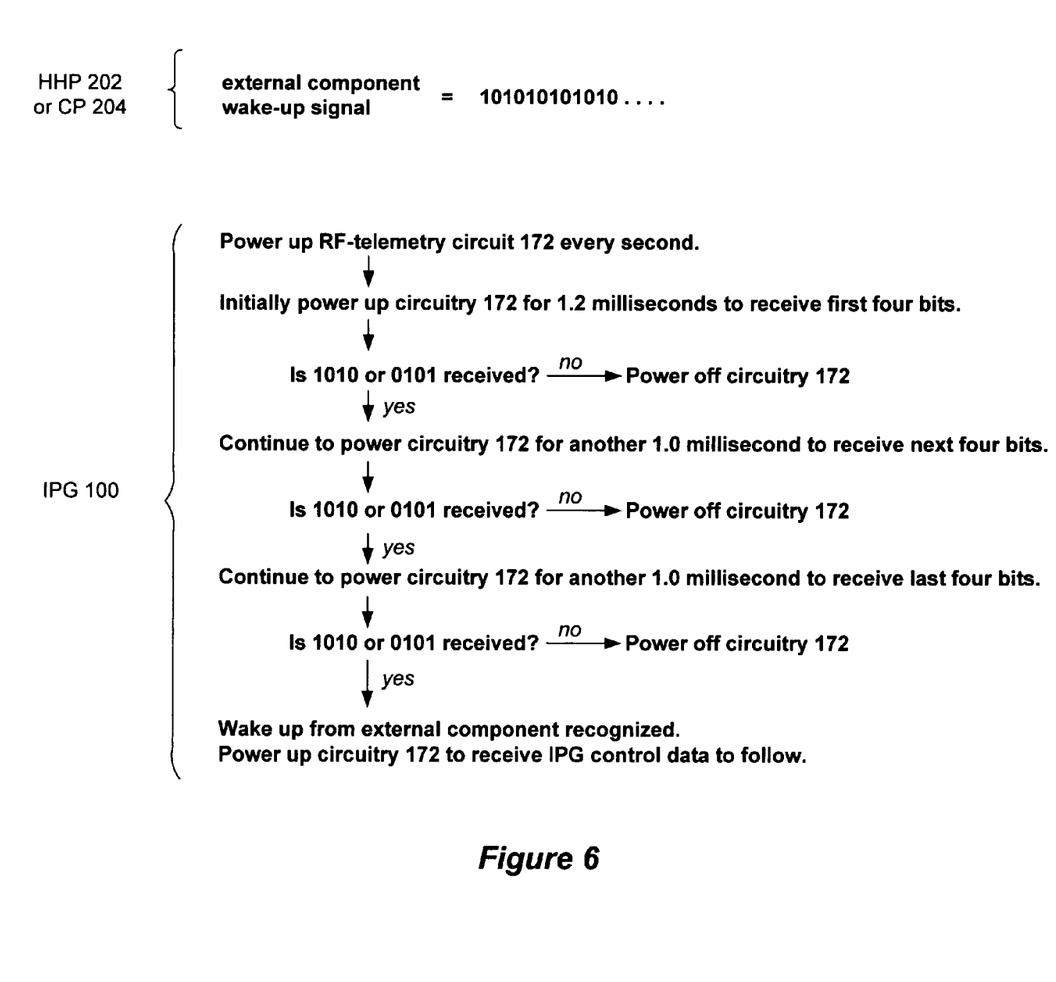
FIG. 6 shows a flow chart of an embodiment of the invention in which the telemetered wake-up signal from an external component is assessed by the IPG in window portions, with a determination of whether to continue powering on the telemetry circuitry being made after assessment of each received window portion.

A basic embodiment of this telemetry circuitry power-on scheme is described with respect to FIG. 6. For purposes of illustration, assume that the wake-up signal from the external component that the IPG 100 must recognize comprises a binary sequence of 12 alternating bits—e.g., 101010101010. In other words, this bit sequence is that which the IPG 100 must recognize as indicative of an external component wishing to communicate, and accordingly the bit sequence that mandates that the IPG 100 fully enable power to the RF-telemetry circuitry 172 to receive data from the external component. As noted earlier, this wake-up signal is preferably broadcast from the external component.

In one embodiment, the IPG 100 breaks its power-on window—i.e., the small window of time each second or so during which the IPG turns on the RF-telemetry circuitry to "listen" for a wake-up signal—into portions to assess the wake-up signal being broadcast (if any) in pieces. More specifically, in an exemplary embodiment, the 12-bit sequence is broken up by the IPG 100 into three partial windows, each comprising 4 bits. Thus, and as FIG. 6 illustrates, instead of the EPG 100 assessing receipt of the entirety of the 12-bit sequence (101010101010), it instead assess only a first portion of this sequence in a first partial power-on window. If the received sequence does not match the first part of the wake-up signal, the IPG 100 powers off the RF-telemetry circuitry 172, which preferably is not again powered until the opening of the window (e.g., about one second later). However, if the IPG understands this partial sequence to be the first part of the external component's wake-up signal (e.g., 1010), it continues to power the RF-telemetry circuitry 172 to receive another 4-bit sequence. Assuming the IPG understands this next partial sequence to match the next part of the wake-up signal (e.g., 1010), it then continues to power on the RF-telemetry circuitry 172 to receive and assess the next (last) portion; else, it powers off the circuitry 172.

In other words, the wake-up signal from the external component is assessed in pieces, and the IPG 100 can expeditiously shut down power to the RF-telemetry circuitry 172 when it becomes apparent that the IPG is not receiving a valid wake-up signal. For example, suppose in the first window portion the IPG receives a code of 0000 (indicating no broadcast from the external component) or a code of 1011 (an erroneous code, perhaps caused by noise). In either case, on just the strength of these four bits, the IPG 100 makes the determination that the wake-up signal is not valid, and hence that the RF-telemetry circuitry 172 can be powered off because there is no point in continuing to waste power in listening for external broadcasts. The result in this example is that the power-on window for the RF-telemetry circuitry 172 is only powered about a third of the time it would be were the entirety of the erroneous broadcast (if any) needlessly received. When it is noted that it is relatively rare for an external component to wish to communicate with the IPG, the exemplary implementation described would on average reduce needless power losses due to powering of the RF-telemetry circuitry 172 to one-third-a significant power savings.

The same is true should an error be determined in the second window portion. For example, suppose the IPG 100 recognized receipt of 1010 in the first window portion, and thus kept power on to RF-telemetry circuitry 172 to receive and assess a second window's portion of data. If in the second window portion an erroneous code were received (e.g., 0010), power to the RF-telemetry circuitry 172 would be terminated at the end of the second window portion, such that a third (last) window portion of data is not needlessly assessed. In this case, more power is consumed than when the failure is found to have occurred during the first window portion, but still power is saved in comparison to a scheme in which the IPG powers the RF-telemetry circuitry 172 for the entirety of the 12-bit period. Moreover, because a relatively high number of bits for the wake-up signal can be used without the necessity of powering on the RF-telemetry circuitry 172 for the entirety of time taken to decode those bits in every instance, telemetry error rates can be kept very low while maintaining improved levels of power consumption.

Assuming that each bit in the wake-up signal is approximately 250 microseconds long, each of the 4-bit window portions is preferably about 1 milliseconds long. (The first window is preferably slightly longer than the others to allow time for the receiver circuitry to stabilize. In addition, other data rates are feasible and included within the scope of the invention.) When the window is first opened, it is unknown whether the external component is transmitting a '1' or a '0', and two sequences are valid: 1010 and 0101. If either valid sequence is detected, the window is extended for another 4-bit window portion (approximately 1 millisecond), at which time a valid sequence is received if it matches the bit sequence that was received in the first window portion. In a preferred embodiment, if a valid (matching) sequence is received, the window is extended for another 4-bit window portion, and the sequence received is again checked for a match with the first two sequences received.

In a preferred embodiment, the flow of FIG. 6 is implemented in software, i.e., by programming the microcontroller 160 of the IPG (see FIG. 3), a task well within one skilled in the art of programming implantable stimulators. In other words, in a preferred embodiment, special circuitry (hardware) is not needed to implement the invention over and beyond what is typically already present in an IPG. However, to further illustrate an embodiment of the invention, FIG. 7 discloses a basic circuit useable to implement the power-reduction telemetry flow of FIG. 6. An actual implementation would have other circuitry features or modifications which are not noted, but would be within the purview of one skilled in the art. Thus, this circuitry is merely illustrative and intended to illustrate operation of an embodiment of the invention at a high level.

Figure 7:
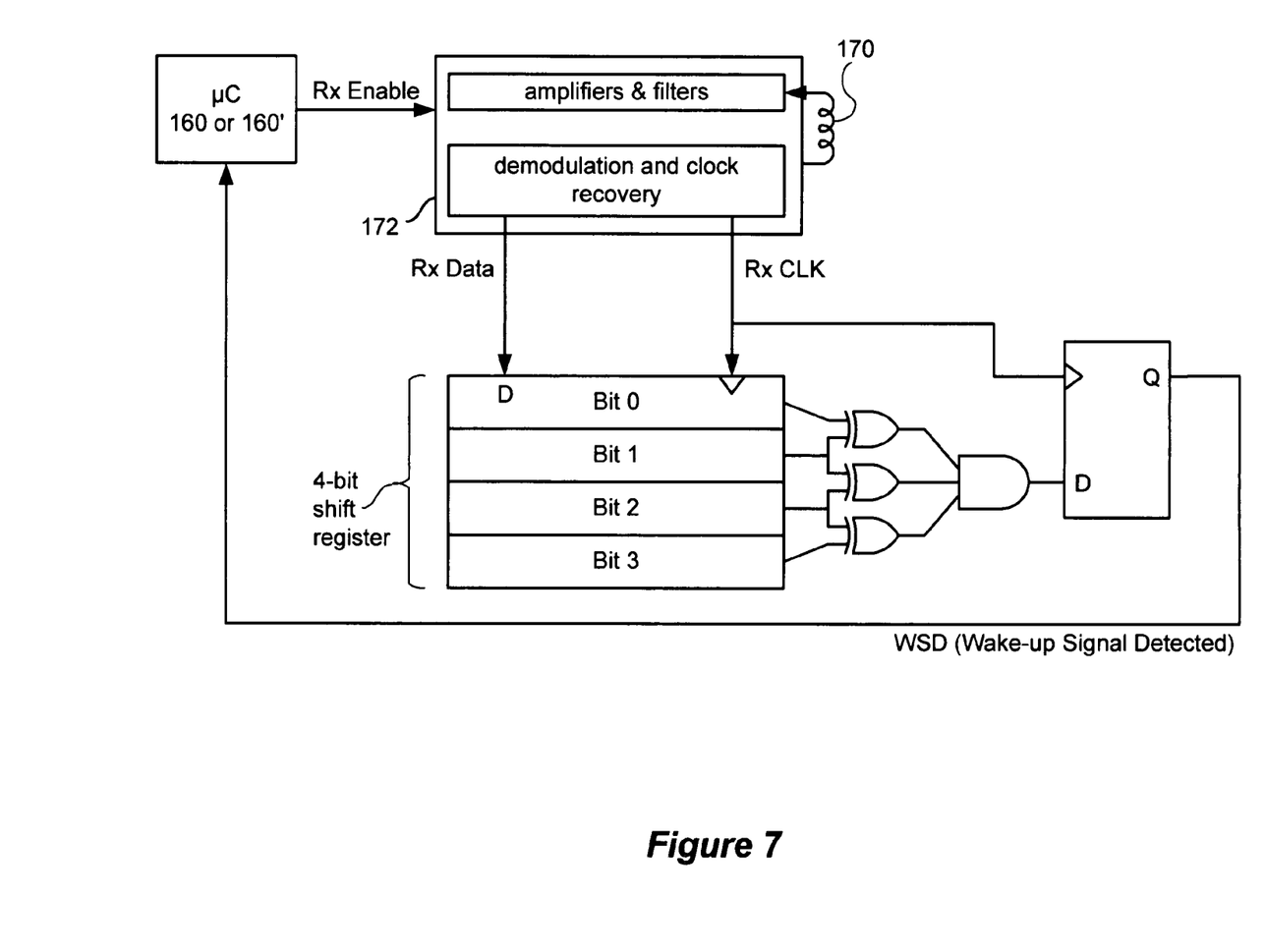
FIG. 7 illustrates an example of hardware useable to implement the process of FIG. 6.

As shown, the receive enable signal (Rx Enable) goes high every second, which also enables (i.e., powers on) the receiver amplifiers, demodulation circuits, clock recovery circuits, etc. It is preferred that the enable signal is initially asserted high (i.e., every second) for at least 1.2 milliseconds, a time sufficient to receive the first four bits (4×250 microseconds) with the additional time used to stabilize the circuitry as noted earlier. Because each of the bits are broadcast for a time period of about 250 microseconds, the clock signal (Rx CLK) would preferably have this same period. The clock signal shifts the received bits into a shift register and successive bits are compared with each other via various logic gates, such as the XOR gates and AND gate shown. The microcontroller waits enough time for 4 bits to be received and then starts to monitor the output of the D Flip Flop, WSD (Wake-up Signal Detected). By virtue of the logic gates, WSD will be high if either valid pattern 1010 or 0101 is stored in the shift register. If WSD is low after having received 4 bits, the microcontroller disables the enable signal, which immediately disables the telemetry circuitry 172 to save power, for example, by effectively disconnecting the telemetry circuitry from its power supply. If WSD is high after 4 bits, but goes low at any time while receiving the next 8 bits, the telemetry circuitry is disabled as soon as WSD goes low. If WSD is high for 12 bit times, the wake-up signal is considered valid and the microcontroller sends a wake-up acknowledgement to the external device when the wake-up signal ends. The microcontroller then prepares to receive data from the external device. Again, it is important to stress that the circuitry of FIG. 7 is merely one example of hardware for implementing an embodiment of the invention. Other hardware or software methods for implementing the flow of FIG. 6 are possible and within the scope of understanding of one skilled in the art having the benefit of this disclosure.

Now that basic features of one embodiment of the telemetry-based improvement to an implantable stimulator have been set forth, it should be noted that other variations and embodiments are possible.

For example, in the preferred embodiment, the wake-up signal the IPG recognizes is 12 alternating bits, e.g., 101010101010. However, alternating bits need not be used, and instead other sequences can be used for the wake-up signal, such as other patterns (e.g., 011001100110), or random sequences (e.g., 110101100001). In either case, the IPG 100 in embodiments of the invention preferably still breaks the power-on window into portions, and assesses each portion sequentially before deciding to continue to power on the RF-telemetry circuitry 172 for the next portion, etc. With a random pattern, the assessment of each window portion would require consideration of different window sequences, but receiving such different sequences and comparing them to expected sequences is easily handled by the logic of the IPG 100 in which the various windows portion patterns would be stored. It should be noted that when non-alternating wake-up patterns are used, more patterns will need to be considered as valid versions of the sequence, thus raising the probability of false detection of the wake-up signal. For example, if the wake-up pattern is 0110, then there are other sequences that the IPG must recognize as potentially valid, i.e., 1100, 1001, and 0011. The fact of other possible valid sequences raises the possibility of error, particularly if noise is an issue. Moreover, use of other patterns will increase the complexity of the logic gates used in FIG. 7. Despite this, non-alternating patterns and/or random sequences can be used in other useful embodiments.

Also, the length of the wake-up sequence can also be varied to be more or less than 12 bits, and the length and number of bits in each window portion can be different from four. In fact, in one embodiment, each window portion can comprise only a single bit. In effect, a one-bit window comprises an approach in which a decision whether to continue powering on the RF-telemetry circuitry 172 is made after each bit is received. Of course, assessing a single bit at a time would be more prone to error than an assessment of a plurality of bits in each window portion, which might not be acceptable in some useful embodiments of the invention.

Although disclosed as comprising an assessment of three window portions, more or less than three windows can be used. Additionally, while it is preferred for simplicity that each window portion comprises the same number of bits, the various window portions can be of different sizes.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A method for enabling communication of data from an external component to an implantable medical device including handling a wake-up signal at the implantable medical device being broadcast from external component, the wake-up signal comprising a plurality of sequential bits, the method comprising:
    powering a receiving circuit in the implantable medical device which receives the wake-up signal;
    receiving a first potion of the wake-up signal at the implantable medical device;
    assessing the validity of the received first portion at the implantable medical device;
    if the received first portion is assessed as valid, continuing to power the receiver circuit to receive at least a second portion of the wake-up signal at the implantable medical device, wherein the first and second portions are identical;
    if the received first portion is assessed as not valid, powering off the receiver circuit; and
    without receiving any further transmissions from the external component not identical to the identical first and second portions, sending an acknowledgment to the external component when the received second portion is assessed as valid while continuing to power the receiver circuit to enable receipt of data to be transmitted by the external component.

2. The method of claim 1, wherein the method is performed periodically.

3. The method of claim 1, wherein the wake-up signal comprises a plurality of sequential bits of alternating logic states.

4. The method of claim 1, wherein the first and second portions of the wake-up signal comprise a plurality of the sequential bits.

5. The method of claim 1, wherein the receiving circuit comprises an antenna and demodulation circuitry.

6. The method of claim 1, wherein the receiving circuit in the implantable medical device receives the portions of the wake-up signal wirelessly from the external component.

7. The method of claim 1, wherein the received second portion is at least one bit.

8. A method for enabling communication of data from an external component to an implantable medical device including handling a wake-up signal comprising a plurality of identical portions sent to the implantable medical being broadcast from the external component, the wake-up signal comprising a plurality of portions, the method comprising:
    (a) periodically powering a receiving circuit in the implanted medical device;
    (b) receiving a portion of the wake-up signal at the powered receiving circuit;
    (c) if the received portion is valid, continuing to power the receiver circuit to receive a next identical portion of the wake-up signal at the receiving circuit, but if the received portion is assessed as not valid, powering off the receiver circuit until the next period;
    (d) repeating step (c) on the received next portion until a last of the plurality of identical portions have been received; and
    (e) without receiving any further transmissions from the external component not identical to the identical portions, sending an acknowledgment to the external component when the received last portion is assessed as valid while continuing to power the receiver circuit to enable receipt of data to be transmitted by the external component.

9. The method of claim 8, wherein each portion of the wake-up signal comprises a plurality of sequential bits of alternating logic states.

10. The method of claim 8, wherein the receiving circuit comprises an antenna and demodulation circuitry.

* * * * *